US008175843B2

(12) United States Patent
Kubiak et al.

(10) Patent No.: US 8,175,843 B2
(45) Date of Patent: May 8, 2012

(54) COMPUTER-IMPLEMENTED METHODS FOR EVALUATING, SUMMARIZING AND PRESENTING DATA ON STABILITY OF DRUG SUBSTANCES AND DRUG PRODUCTS AND SOFTWARE-MODIFIED COMPUTERS FOR SUCH METHODS

(75) Inventors: Rene Kubiak, Assmannshardt (DE); James Schwenke, New Milford, CT (US); Volker Krzykalla, Ummendorf (DE); Hans-Juergen Lomp, Mittelbiberach (DE); Cornelia Schepers, Mainz (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 653 days.

(21) Appl. No.: 12/292,288

(22) Filed: Nov. 14, 2008

(65) Prior Publication Data

US 2010/0125434 A1    May 20, 2010

(51) Int. Cl.
*G06F 17/18* (2006.01)
(52) U.S. Cl. .................. 702/179; 702/19; 705/2; 705/3; 703/12
(58) Field of Classification Search .................... 702/19, 702/179; 705/2, 3; 703/12
See application file for complete search history.

(56) References Cited

U.S. PATENT DOCUMENTS

| 6,532,427 | B1 * | 3/2003 | Joshi et al. ....................... 702/84 |
| 6,766,319 | B1 * | 7/2004 | Might .................................. 1/1 |
| 6,925,391 | B1 * | 8/2005 | Pesce et al. ...................... 702/21 |
| 7,469,390 | B2 * | 12/2008 | Mickle et al. ................. 716/103 |
| 2003/0158670 | A1 * | 8/2003 | Hougaard ....................... 702/19 |
| 2006/0031022 | A1 * | 2/2006 | Hougaard ....................... 702/19 |
| 2007/0022142 | A1 * | 1/2007 | Palmer et al. ................. 707/200 |

FOREIGN PATENT DOCUMENTS

JP    2000010793 A  *  1/2000

OTHER PUBLICATIONS

Krzykalla, Volker et al. "BIGSTEP: Boehringer Ingelheim Global Stability Testing Evaluation Program User's Manual Version 1.1." Boehringer Ingelheim (2005): 1-138.

* cited by examiner

*Primary Examiner* — Carol Tsai
(74) *Attorney, Agent, or Firm* — Michael P. Morris; Mary-Ellen M. Devlin

(57) ABSTRACT

Computer-implemented methods for statistical analysis and summarization of a stability study on a pharmaceutical product using of a macro integrated into statistical analysis software. The method includes inputting and summarizing data observed for a stability study on a pharmaceutical product, statistically analyzing the data, including using at least one regression function to characterize the time-response relationship of at least one stability response variable, to estimate a shelf life of the pharmaceutical product or confirm the shelf life of an existing pharmaceutical product, and providing standardized output data and graphical presentations of observed stability response data. Also, a computer loaded with a general statistical analysis software and a macro integrated with the software such that the computer is capable of performing these computer-implemented methods using the software and macro.

36 Claims, 2 Drawing Sheets

COMPUTER-IMPLEMENTED METHODS FOR EVALUATING, SUMMARIZING AND PRESENTING DATA ON STABILITY OF DRUG SUBSTANCES AND DRUG PRODUCTS AND SOFTWARE-MODIFIED COMPUTERS FOR SUCH METHODS

Reference is hereby made to a computer program listing appendix submitted on a compact disc for this application. An identical duplicate disc is also submitted. A total of two compact discs are filed each of which contains the following files:

| File Name | Size | Date of Creation |
| --- | --- | --- |
| _bs_sub_alloc_vars.rtf | 9 KB | 4/13/2006 |
| _bs_sub_calc_dd.rtf | 15 KB | 4/13/2006 |
| _bs_sub_calc_pp.rtf | 24 KB | 4/13/2006 |
| _bs_sub_calc_pp_ancova.rtf | 11 KB | 4/13/2006 |
| _bs_sub_calc_pt.rtf | 25 KB | 4/13/2006 |
| _bs_sub_calc_sl.rtf | 13 KB | 4/13/2006 |
| _bs_sub_calc_kr.rtf | 9 KB | 4/13/2006 |
| _bs_sub_calculations.rtf | 98 KB | 4/13/2006 |
| _bs_sub_create_ds_modelways.rtf | 51 KB | 4/13/2006 |
| _bs_sub_create_ds_titlechecks.rtf | 7 KB | 4/13/2006 |
| _bs_sub_create_ds_validmodels.rtf | 31 KB | 4/13/2006 |
| _bs_sub_disp_control.rtf | 115 KB | 4/13/2006 |
| _bs_sub_expand_ds_af.rtf | 5 KB | 4/13/2006 |
| _bs_sub_get_const.rtf | 3 KB | 4/13/2006 |
| _bs_sub_graph.rtf | 63 KB | 4/13/2006 |
| _bs_sub_indata.rtf | 31 KB | 4/13/2006 |
| _bs_sub_indata_attr.rtf | 22 KB | 4/13/2006 |
| _bs_sub_indata_const.rtf | 9 KB | 4/13/2006 |
| _bs_sub_indata_graphs.rtf | 17 KB | 4/13/2006 |
| _bs_sub_indata_groups.rtf | 46 KB | 4/13/2006 |
| _bs_sub_initial.rtf | 24 KB | 4/13/2006 |
| _bs_sub_message.rtf | 33 KB | 4/13/2006 |
| _bs_sub_meta_file.rtf | 47 KB | 4/13/2006 |
| _bs_sub_meta_file_gr.rtf | 11 KB | 4/13/2006 |
| _bs_sub_mod_func.rtf | 9 KB | 4/13/2006 |
| _bs_sub_model_calc.rtf | 49 KB | 4/13/2006 |
| _bs_sub_out_graph.rtf | 47 KB | 4/13/2006 |
| _bs_sub_out_graph_cal.rtf | 12 KB | 4/13/2006 |
| _bs_sub_parm_check.rtf | 37 KB | 4/13/2006 |
| _bs_sub_placeholder.rtf | 37 KB | 4/13/2006 |
| _bs_sub_prepare_calc.rtf | 9 KB | 4/13/2006 |
| _bs_sub_rep_modeltrans.rtf | 6 KB | 4/13/2006 |
| _bs_sub_rep_zerofill.rtf | 7 KB | 4/13/2006 |
| _bs_sub_report.rtf | 39 KB | 4/13/2006 |
| _bs_sub_resolve_parms.rtf | 16 KB | 4/13/2006 |
| _bs_sub_shrink_dataset.rtf | 5 KB | 4/13/2006 |
| _bs_sub_single_check.rtf | 64 KB | 4/13/2006 |
| _bs_sub_start_vals.rtf | 22 KB | 4/13/2006 |
| _bs_sub_system_defaults.rtf | 10 KB | 4/13/2006 |
| _bs_sub_title_check.rtf | 24 KB | 4/13/2006 |
| _bs_sub_value_in_list.rtf | 11 KB | 4/13/2006 |
| _bs_sub_y_scaling.rtf | 11 KB | 4/13/2006 |
| _xx_entimo_check_file_exist.rtf | 6 KB | 4/13/2006 |
| _xx_entimo_check_file_read.rtf | 5 KB | 4/13/2006 |
| _xx_entimo_check_fileref.rtf | 5 KB | 4/13/2006 |
| _xx_entimo_check_library_exist.rtf | 4 KB | 4/13/2006 |
| _xx_entimo_check_num_value.rtf | 10 KB | 4/13/2006 |
| _xx_entimo_check_quoted.rtf | 6 KB | 4/13/2006 |
| _xx_entimo_check_sas_aspects.rtf | 61 KB | 4/13/2006 |
| _xx_entimo_cnt_quoted_items.rtf | 4 KB | 4/13/2006 |
| _xx_entimo_delete_in_library.rtf | 3 KB | 4/13/2006 |
| _xx entimo descr stats.rtf | 41 KB | 4/13/2006 |
| _xx_entimo_export_data.rtf | 8 KB | 4/13/2006 |
| _xx_entimo_get_extract.rtf | 4 KB | 4/13/2006 |
| _xx_entimo_get_qitem.rtf | 6 KB | 4/13/2006 |
| _xx_entimo_get_unique_list.rtf | 5 KB | 4/13/2006 |
| _xx_entimo_import_data.rtf | 7 KB | 4/13/2006 |
| _xx_entimo_print_parm.rtf | 6 KB | 4/13/2006 |
| _xx_entimo_sel_excl.rtf | 14 KB | 4/13/2006 |
| _xx_entimo_start_stop.rtf | 8 KB | 4/13/2006 |
| _xx_entimo_string_with_delim.rtf | 7 KB | 4/13/2006 |
| _xx_entimo_unquote.rtf | 4 KB | 4/13/2006 |
| _xx_entimo_update_string.rtf | 9 KB | 4/13/2006 |
| _xx_entimo_wordcount.rtf | 7 KB | 4/13/2006 |
| Version.rtf | 1 KB | 4/13/2006 |

The material in the compact disc is hereby incorporated-by-reference into this application.

Pharmaceutical products must be intensively tested to guarantee high safety for patients. Quantifying the stability of a drug to define a shelf life is one of the objectives. A statistical analysis of stability studies on pharmaceutical products can be conducted using analyses of covariance techniques by fitting confidence intervals for mean responses represented by regression lines or curves. Several time-consuming steps are involved in these analyses, including the preparation of result tables and graphs. From the ICH (International Conference on Harmonization, June 2004), guideline Q1E sets forth the needed statistical analyses for stability studies and the invention is particularly provided as a means for complying with this guideline.

The invention provides a validated system of computer-implementable programming for use together with statistical analysis software. For example, the programming can be used with SAS® Version 8.2 system software, higher versions of this software or software which performs ; essentially the same functions as this software. Validated means that checks and tests were performed to be sure that everything works as it was defined in the user requirements document. The programming is preferably in the form of a macro that is usable with the base statistical analysis software. A computer loaded with the base statistical analysis software and a macro according to the invention can be used for the evaluation and summarization of data obtained from one or more stability studies on a pharmaceutical product. This invention allows standard as well as non-standard statistical analysis steps to be conducted automatically. It transforms the raw data into a useful display of the results which are preferably summarized in Word® format for insertion into a statistical or study report. Because of the automatic transfer of all output tables and graphs to Word® the invention reduces the time needed to evaluate the data. The invention also greatly reduces the handling, checking, and report preparation efforts. The invention results in harmonizing the statistical evaluations which are conducted and also the resulting report tables and graphs. The result is a uniform presentation of stability data in stability study reports. Such evaluated and presented results are particularly useful for submission to regulatory agencies (e.g., the FDA) for drug product approval. Thus, the invention is useful for facilitating and speeding internal processing of stability studies of drug products but also the regulatory agency review thereof.

The invention can be used for all statistical analyses of stability data, including, for example, testing due to variation on the market authorization, such as that required for registration purposes, and on an ongoing basis for all commercial products. It can also be used to support stability testing for different types of drugs (e.g., drug substances or drug products) as well as the status of the drugs' life cycles (e.g., first marketing authorization application or changes post approval). It can be used, for example, to establish a retest period or to support or extend a proposed retest period for a drug substance or a shelf life for a drug product.

The system provided by the invention is a validated system that can be used for several stability study designs and time-response relationships and meets all regulatory requirements. Thus, not only standard designs and approaches are implemented to be analyzed comfortably and quickly, but also solutions which are not described in the literature for non-standard designs.

The macro programming of the invention is designed to be user-friendly with a standard statistical analysis software program, e.g., SAS® Version 8.2. The language and commands used with the statistical analysis software are sufficient to control the macro of the invention. The macro of the invention connects the data to be analyzed and defines particular options for statistical stability analyses as well as table and graph output requirements. Thus, various analysis, output, and layout options can be specified, allowing for a variety of stability studies and layout designs to analyze data from several response variables and storage conditions with one run.

Examples of the general advantages of the invention include the following:
- performing all standard statistical analyses need for drug stability studies: including: attributes (e.g., assay, impurities); additional factor levels (e.g., levels of storage orientation like 'Upright' and 'Inverted'); Storage conditions (e.g., 25° C./60% RH, 30° C./70% RH); and By-variables (combinations of the levels of different by-variables are called by-gro),
- presentation of individual data and summary statistics;
- comparing of different time-response relationships,
- model selection by pooling of batches and additional factor levels, use of common release data in pooling process and use of different time-response relationships in pooling process,
- pre-testing to determine if a formal statistical analysis is necessary,
- shelf-life calculations with one- or two-sided confidence or prediction intervals and support of proposed shelf life,
- transfer of all result tables and graphs automatically into MS Word® format,
- defining of all details for table layout, graph layout, and statistical evaluation by the user;
- short runtime; and
- a validated system.

Other optionally applicable advantages include the following non-standard statistical analyses:
- six non-linear time-response functions can be compared graphically and in a table that lists the functions ranked by the best fitting,
- in addition to a three model approach, a theoretical possible fourth model can be included into the analysis,
- a pre-test to check if a formal statistical analysis is necessary can be conducted,
- Four non-linear functions (Simple Linear, Quadratic, Two exponential Functions) can be used for statistical evaluation,
- a model selection/pooling process—if an additional factor should be considered for pooling—can be defined on basis of analysis of covariance techniques and implemented,
- common or individual release data can be considered in statistical model,
- two different model selection approaches (on full or reduced model) can be used for standard or non-standard evaluations.

The following description is provided as an example for installing and running a specific macro, called BIGSTEP, into a SAS® statistical analysis program to provide a system for carrying out the invention. A copy of the User's Manual for BIGSTEP is filed with the application and is incorporated by reference into this application. Further, the computer code for the BIGSTEP macro is provided as a computer program listing appendix in the discs, as discussed above. It is to be understood, however, that this is only an example of one embodiment of the invention and the invention is not limited to this specific description. For example, according to the invention, a different macro for performing substantially the same steps could be provided for performing the invention in connection with a statistical analysis program, including programs other than the SAS® program.

The macro for carrying out the invention can be installed by simply copying a few files to a directory or subdirectory of the user's choice. In addition to the five system and system parameter default files, the macro is called and run through the statistical analysis program SAS®, which includes the option statements required for a particular stability analysis. In particular, this SAS® product contains Base SAS, SAS/ASSIST, SAS/ETS, SAS/GRAPH, SAS/IML and SAS/STAT. For example, SAS® Version 8.2 provides these components and higher versions of this software or software which performs essentially the same functions as this software could also be used. Finally, a dataset is used, which is to include the stability dataset to be statistically analyzed.

Five SAS® files that contain the BIGSTEP macro program code and system default options are to be copied into the directory in which the program is provided. These files are:
SASMACR.SAS7BCAT
DEFAULTS.SAS7BDAT
CONSTANTS.SAS7BDAT
GRAPHS.SAS7BDAT
BIGSTEP.DOT SASMACR.SAS7BCAT is a SAS® catalog that contains the SAS® code defining the BIGSTEP program. This file should not be opened or altered by the user for any reason. The BIGSTEP program is written as a series of macros, which are SAS® subroutines or programs that are called through a macro call in an analysis program by specifying the BIGSTEP statistical analysis and summary output options.

DEFAULTS.SAS7BDAT, CONSTANTS.SAS7BDAT, and GRAPHS.SAS7BDAT are SAS® datasets, which contain background settings as further explained below. The Word® template file BIGSTEP.DOT contains the document settings for transfers of all BIGSTEP output to Word® using A4 or Letter sized paper.

The next steps are to create an analysis environment, the stability data file, and the stability analysis program file to conduct a statistical analysis of a stability study as detailed below. Through a user-defined analysis SAS® program file, stability data are processed as a SAS® dataset, a variety of statistical analyses are performed for different study designs and response variables, and summary output tables and graphs are produced in Word® format. The analysis program file is submitted to SAS® in either batch mode or in an interactive session.

BIGSTEP provides a standardized methodology and presentation format for the statistical analysis and summarization of a stability study. BIGSTEP has three major purposes:
- summarize data observed for a stability study,
- provide the statistical support for estimating a shelf life of a new drug,
- provide the statistical support for confirming the shelf life of an existing drug.

BIGSTEP provides standardized output data listings and graphical presentations of observed stability response data. Summary tables and graphs can be output in a format suitable for Word® documents.

BIGSTEP provides a complete statistical analysis of stability response data for estimating the shelf life of a new pharmaceutical compound, allowing the fitting of various regression functions to characterize the time-response relationship of a response variable. A statistical analysis is provided to test the consistency of response among different batches and among the levels of an additional study factor; such as product orientation or product packaging. Based on user supplied specification limits or acceptance criteria, a shelf life is estimated for the best fitted or user defined regression function, allowing for pooling of batch or additional study factor response data.

BIGSTEP provides a complete statistical analysis of stability response data for confirming or supporting the proposed shelf life of a marketed pharmaceutical product. Following ICH guidelines, batch response is evaluated to determine if the proposed shelf life can be supported. If not, a statistical analysis similar to that conducted to estimate a shelf life is performed.

BIGSTEP provides a standardized statistical analysis of data from a stability study. The statistical analysis is controlled by setting various options in the SAS® analysis program including the BIGSTEP macro call. FIG. 1 is a schematic flow chart of the BIGSTEP analysis. There are three sections to a BIGSTEP analysis:

| | |
|---|---|
| INPUT: | Parameter and data verification |
| ANALYSIS: | Statistical analysis |
| OUTPUT: | Output of result tables and graphs |

In the input or verification phase of a BIGSTEP analysis, internal program checks are made on the analysis program and the DEFAULTS dataset. If an error is detected, the analysis is stopped and an error message is reported. The analysis dataset, here called STABILITY for convenience, in addition to the BIGSTEP system datasets CONSTANTS and GRAPHS and the system input datasets ATTRIBUTES and GROUPS are verified.

Once the input datasets are verified, the analysis phase begins. Through the setting of various analysis options and parameters in the BIGSTEP analysis program, several different analysis objectives can be achieved. There are five major analysis components to the BIGSTEP analysis:

| | |
|---|---|
| DD: | Data Description |
| TR: | Time Response regression model |
| PP: | Pooling Process for regression model |
| PT: | Pre-Test evaluation |
| SL: | Shelf Life estimation |

The Data Description (DD) component provides for data listings, summary statistics, and plots of the observed data. The Time Response (TR) component allows for investigating different regression model fits to the observed response data. Summary information is provided through tables and graphical displays. The Pre-Test (PT) is a statistical evaluation to determine if there is a significant change in response over storage time. If a significant change in response over storage time is detected, a full stability analysis is then conducted through BIGSTEP. If a significant change in response over storage time is not detected, a simple scatter plot of the response data is produced. The first step in a stability statistical analysis is to determine the best fitted regression model to be used to characterize response. Depending on the type of regression model selected by the user, a statistical Pooling Process (PP) is conducted to determine if differences among batch (or lot) response or differences among the categories of the additional study factor (if an additional study factor was considered in the stability study) can be detected. If differences in response cannot be detected the data among batches and/or the additional study factor are pooled together and characterized by a more simple regression model. The stability statistical analysis is concluded by estimating a Shelf Life (SL) based on the appropriate regression model.

The results of the stability statistical analysis are reported through the output phase of the BIGSTEP analysis. The format and content of the various summary tables and graphical displays are controlled through various options and parameters, set in the BIGSTEP analysis program. Summary results can be displayed on the computer screen or saved as files in either list, RTF or Word® formats. Results saved in either RTF or Word® formats are suitable for insertion into formal stability study summary reports.

The basic stability design follows one or more potentially stability-limiting response variables (i.e., assay of active ingredient, water content, impurities) over time, where the pharmaceutical product of interest is being stored in environmentally stable conditions to meet regulatory guidelines. The duration of a stability study is typically between 6 months to 36 months. Usually 3 to 6 batches or lots of the product are included in the stability study with a pre-defined sampling scheme used to observe response to storage time. The overall goal of a stability study is to either estimate or confirm a pharmaceutical product's shelf life.

A stability study may involve more than one environmental storage condition being considered simultaneously. However, common practice has the response data from each storage condition being statistically analyzed separately. This is because the typical objective of a stability study is not to compare response among storage conditions, but rather to characterize response for each storage condition to estimate or confirm a shelf life. It will be assumed throughout this disclosure that the statistical analysis of one storage condition is being discussed.

As noted above, the basic stability study follows the effect of storage time on one or more potentially stability-limiting response variables for different batches. A more involved stability study also considers the effect of an additional study factor or treatment factor, such as product orientation (upright, inverted or side storage) or packaging type (bottles or blister packs), on sample response. In these more involved studies, there are two designs that can be statistically analyzed through BIGSTEP. The two study designs are defined by how the initial, or Storage Time 0, sample response data are obtained. The first study design, conveniently referred to as the independent sampling design, has an independent sample being measured at Time 0. For example, considering a stability study where product storage orientation is also of interest, samples stored upright and samples stored in an inverted orientation are independently measured for response at Time 0, for each batch or lot. Alternatively, the second study design, conveniently referred to as the common sampling design, measures response at Time 0 for both the upright and inverted samples, for example, for each batch, while the pharmaceutical product is still in a common state. For example, for ease and practicality of handling the samples or to keep the overall sample size to a minimum, the Time 0 response is measured from the common batch at batch release. (It would be a contrivance, and technically impossible, to measure a response for upright and inverted samples at a true Time 0.) Thus, a single common sample for each batch or lot is measured and recorded for both the upright and inverted Time 0 response.

The statistical issue differentiating between the independent and common sampling designs is one of sample size, and thus, degrees of freedom. Considering the example where storage orientation is an additional factor to be considered in a stability study, the independent sampling stability design would have two samples observed at Time 0 for each batch or lot, corresponding to the upright and inverted storage orientations. However, the common sampling stability design would have only a single sample observed at Time 0 for each batch, with the single sample to be simultaneously used as the Time 0 response for both the upright and inverted storage orientations.

For stability study designs where an additional study factor is considered, independent or common sampling designs are differentiated for a BIGSTEP analysis through appropriately defining the analysis data file.

The statistical analysis of stability study data is based on regression analysis methodology. In regression analysis, a regression model (or function) is defined to adequately characterize the observed data for a particular stability response variable. Four regression models, which have been proven useful for the statistical analysis of stability data, are available through BIGSTEP; simple linear, quadratic, first order exponential and second order exponential models. The details of the statistical analyses conducted through BIGSTEP are discussed in the Users Manual which is incorporated by reference herein.

Finally, the analysis program file calls the BIGSTEP SAS® macro library of programs, the SAS® dataset to be analyzed, and provides the appropriate options for the statistical analysis. The SAS® analysis program file can be named any acceptable SAS® filename and can be saved in any directory convenient for the user. The format of the analysis program file is discussed extensively throughout the User's Manual.

To install BIGSTEP, for example, a directory is created for the BIGSTEP SAS® programs and Word® template C:\BIGSTEP\Program Files\System. To conduct a BIGSTEP analysis of a stability study, it is recommended that a separate directory structure be created for the study data, analysis program and summary results, for each study. This is because any number of stability studies can be statistically analyzed with one installation of BIGSTEP. The separate directory structure is a pragmatic suggestion for maintaining the integrity of the different study data, analysis and result files. One option is to create one additional directory to store the data, analysis and result files together. To demonstrate the options available through BIGSTEP, three additional directories can be created to store the data, analysis and result files separately.

Following the suggestion to create separate directories for the stability study data, analysis program, and analysis results, create a root directory for the stability study. Let the root directory be C:\BIGSTEP\Study, although the root directory name can be anything the user prefers. Under the root directory, for example, create three subdirectories named C:\BIGSTEP\Study\Data, C:\BIGSTEP\Study\Program, and C:\BIGSTEP\Study\Results, for the study data, analysis program, and study results, respectively.

Following the separate directory structure discussed above, C:\BIGSTEP\Study\Data is the subdirectory containing the stability dataset to be statistically analyzed through BIGSTEP. The necessary file format for the dataset for BIGSTEP is as a permanent SAS® dataset. Other file structures, such as an Excel dataset, are acceptable but require additional programming code to read into BIGSTEP.

The data file can be named any appropriate SAS® dataset name, for example, STABILITY_DATA.SAS7BDAT for a Version 8.2 SAS® dataset. The data file is called through the analysis program option IN_DATA. Table 1 is a listing of the variables that can be included in the data file. The particularly preferred variables to be included in the data file are ATTRIBUTE, STORAGE, BATCH, TIME, and LEVEL. The BYVAR variable is included in the data file to allow separate statistical analyses for stability characteristics that are not of interest to be compared statistically, such as product packaging type. The variable FACTOR is included in the data file for those stability studies, which include an additional study factor that is of interest to compare statistically, such as product storage orientation.

TABLE 1

Analysis Dataset Variable Definitions

| Variable | Mandatory | Type | Description | Comments |
| --- | --- | --- | --- | --- |
| BYVAR | no | any | levels of variable to be analyzed separately defined by parameter IN_BY_VARS | values must not be missing |
| ATTRIBUTE | yes | any | name of attribute to be evaluated i.e., 'ASSAY' or 'WATER' | values must not be missing |
| STORAGE | yes | char | storage condition i.e., '25° C./60% RH' | values must not be missing |
| FACTOR | no | char | additional study factor defined by parameter IN_ADD_FACTOR must be consistent with parameter GL_COMMON_RELEASE | values must not be missing if GL_COMMON_RELEASE is YES, the content of the additional factor of time 0 has to be "COMMON" if GL_COMMON_RELEASE is NO, the content of the additional factor of time 0 must to be "COMMON" |

TABLE 1-continued

Analysis Dataset Variable Definitions

| Variable | Mandatory | Type | Description | Comments |
|---|---|---|---|---|
| BATCH | yes | any | batch (or lot) identifier | values must not be missing |
| TIME | yes | num | study sampling times sampling time unit is defined by parameter IN_TIME_UNIT | values must not be missing check for at least two different values for each combination of by-var, attribute, storage condition and additional factor |
| LEVEL | yes | num | value of attribute sample response unit of measurement is defined by parameter IN_LEVEL_UNIT | no data check data may be missing observations with missing values are not deleted automatically |

The analysis dataset variable names listed in Table 1, BYVAR, ATTRIBUTE, STORAGE, FACTOR, BATCH, TIME, and LEVEL, are the default for a BIGSTEP analysis. User-defined variable names can be used in the analysis dataset. However, if variable names other than the default names are used, the user-defined variable names must be designated in the analysis program through the IN_VARS option, and the user-defined names must be used consistently throughout the analysis program. Labels can be assigned to the variables through the analysis dataset.

BIGSTEP does not use any variable formats defined directly to the input dataset. Formats are defined by the user through the VALUE statement in PROC FORMAT. The format name is then specified in the analysis program through the option IN_FORMATS. Formats specified in the IN_FORMATS statement are used for the summary output and output datasets.

Table 2 is an example showing a partial listing of a dataset for a stability study for MDI (Metered Dose Inhaler) canisters stored at 25° C./60% RH. The water content of the canister contents, in parts per million, was measured for several batches over a 24-month study duration. Two canister storage orientations, upright and inverted, were studied using samples from each batch.

TABLE 2

Example Dataset Format for Independent Release Stability Study

| ATTRIBUTE | STORAGE | FACTOR | BATCH | TIME | LEVEL |
|---|---|---|---|---|---|
| ... | | | | | |
| Water | 25° C./60% RH | Inverted | 000103 | 0 | 5049 |
| Water | 25° C./60% RH | Inverted | 000103 | 3 | 5304 |
| Water | 25° C./60% RH | Inverted | 000103 | 6 | 5218 |
| Water | 25° C./60% RH | Inverted | 000103 | 9 | 5327 |
| Water | 25° C./60% RH | Inverted | 000103 | 12 | 5344 |
| Water | 25° C./60% RH | Inverted | 000103 | 18 | 5369 |
| Water | 25° C./60% RH | Inverted | 000103 | 24 | 5394 |
| Water | 25° C./60% RH | Upright | 000103 | 0 | 5055 |
| Water | 25° C./60% RH | Upright | 000103 | 3 | 5124 |
| Water | 25° C./60% RH | Upright | 000103 | 6 | 5186 |
| Water | 25° C./60% RH | Upright | 000103 | 9 | 5249 |
| Water | 25° C./60% RH | Upright | 000103 | 12 | 5229 |
| Water | 25° C./60% RH | Upright | 000103 | 18 | 5347 |
| Water | 25° C./60% RH | Upright | 000103 | 24 | 5523 |
| ... | | | | | |

Other dataset variables (columns) can be added in the data file but will not be used in the analysis. For example, for data recording purposes, a column for sample replicate number could be added if replicate measurements were recorded for each sample.

As discussed above, there are two basic stability study designs for studies involving an additional study factor; independent release designs and common release designs. The different study designs are differentiated by how the initial or Time 0 response is measured for each batch. Table 2 is an example of an independent release design, where a Time 0 response is measured independently for each storage orientation from each batch. Table 3 is an example of a common release design, where the Time 0 measurement was obtained from batch release information and used as the Time 0 response for both the inverted and upright MDI canisters for that batch.

TABLE 3

Example Dataset Format for Common Release Stability Study

| ATTRIBUTE | STORAGE | FACTOR | BATCH | TIME | LEVEL |
|---|---|---|---|---|---|
| ... | | | | | |
| Water | 25° C./60% RH | COMMON | 000103 | 0 | 5049 |
| Water | 25° C./60% RH | Inverted | 000103 | 3 | 5304 |
| Water | 25° C./60% RH | Inverted | 000103 | 6 | 5218 |
| Water | 25° C./60% RH | Inverted | 000103 | 9 | 5327 |
| Water | 25° C./60% RH | Inverted | 000103 | 12 | 5344 |
| Water | 25° C./60% RH | Inverted | 000103 | 18 | 5369 |
| Water | 25° C./60% RH | Inverted | 000103 | 24 | 5394 |
| Water | 25° C./60% RH | Upright | 000103 | 3 | 5124 |
| Water | 25° C./60% RH | Upright | 000103 | 6 | 5186 |
| Water | 25° C./60% RH | Upright | 000103 | 9 | 5249 |
| Water | 25° C./60% RH | Upright | 000103 | 12 | 5229 |
| Water | 25° C./60% RH | Upright | 000103 | 18 | 5347 |
| Water | 25° C./60% RH | Upright | 000103 | 24 | 5523 |
| ... | | | | | |

A stability study statistical analysis is conducted by a call to the BIGSTEP macro library through a SAS® Version 8.2 program. The SAS® program is referred to as the analysis program. The analysis program may be named any appropriate SAS® program file name. It is suggested that the analysis program file name extension should be ".SAS", which is the naming structure expected, but not mandated, by SAS® . Let the analysis program file name be "STABILITY.SAS". Following the proposed directory structure, the analysis program file is to be stored in C:\BIGSTEP\Study\Program.

Table 4 is a listing of the SAS® code for a basic analysis program for conducting a complete stability statistical analysis with the objective of estimating a product shelf life. The data are from a 24-month stability study of Atrovent HFA metered dose inhalers. For mere exemplification, the presented analysis is being limited to four response variables, each of which have potentially stability-limiting characteristics; canister weight loss, total canister assay, canister citric acid content, canister water content.

In this stability study, MDI canisters were stored under two storage conditions; 25° C./60% RH and 30° C./70% RH. For each storage condition, responses to the canister being stored in an upright and inverted orientation were studied. Response was measured at 0, 3, 6, 9, 12, 18, and 24 months of storage. Because of the complexity of defining samples for canisters stored at a storage condition and orientation at Time 0, batch release measurements were used instead. Thus, the response at Time 0 for each batch is the sample recording for both the upright and inverted storage conditions. This defines the common release stability study. A partial data listing for this study is given in Table 3.

The analysis program file, STABILITY.SAS, begins by defining two LIBNAMEs. A LIBNAME is a SAS® statement, which sets a path to a specific directory. LIBNAME DATA points to the directory where the stability data file is stored. LIBNAME BIGSTEP points to the directory where the BIGSTEP macro library is stored.

Two SAS® options are required, given in the OPTIONS statement. MSTORED is a SAS® option that specifies that the macro facility search for stored compiled macros in the SASMACRO catalog of the SAS® data library that is referenced by the SASMSTORE option. SASMSTORE specifies the libref of a SAS® data library that contains, or will contain, a catalog of stored, compiled SAS® macros. This libref cannot be WORK, which is the SAS® default temporary work directory.

In the example, three temporary SAS® datasets are used for a BIGSTEP analysis; RESPONSES (with data from permanent dataset STABILITY_DATA), ATTRIBUTES, and GROUPS. These temporary datasets are defined for the current BIGSTEP analysis in the analysis program and are resident in memory only during the current BIGSTEP session. A SAS® dataset with the stability data and the ATTRIBUTES dataset are necessary and have to be defined by the user. The GROUPS dataset is optional and is not always necessary.

For the three mandatory background SAS® datasets CONSTANTS, DEFAULTS, and GRAPHS the permanent default data sets are used for this BIGSTEP analysis. These datasets are stored in the same directory as the BIGSTEP macro library and are automatically reference by the BIGSTEP program through LIBNAME BIGSTEP. As discussed in the following sections it is usually not necessary to change them.

The stability analysis dataset to be statistically analyzed must be a permanent SAS® dataset, stored in a convenient directory. If the analysis dataset requires no further data management, it can be specified directly through the IN_DATA and IN_DATA_PATH options in the % BIGSTEP call to the macro library, for example, IN_DATA_PATH=C:\BIGSTEP\STUDY\DATA and IN_DATA=STABILITY_DATA, following the example analysis dataset name defined above. Of course, the analysis dataset can be named any acceptable SAS® dataset name. Alternatively, the directory the analysis dataset is stored in can be referenced through, e.g., LIBNAME DATA, with the IN_DATA option in the % BIGSTEP call being IN_DATA=DATA.STABILITITY_DATA.

If further data management is required prior to analysis, such as setting variable labels or partitioning the dataset, the analysis dataset can be defined through a data step. The temporary analysis dataset defined through the data step can be named any acceptable SAS® dataset name. A data step is used to define the analysis dataset, RESPONSES, in the example analysis program listed in Table 4. Using the study analysis dataset STABILITY_DATA, labels are defined for the dataset variables to be used in the BIGSTEP analysis. Further data MANAGEMENT may be conducted through the data step. For example, because BIGSTEP analyzes all response variables included in the analysis dataset, the study analysis dataset may be partitioned to include only a selection of the response variables. RESPONSES is then specified as the analysis dataset through the IN_DATA option in the % BIGSTEP call as IN_DATA=RESPONSES.

The ATTRIBUTES dataset that has to be defined by the user contains the information about the characteristics of the attributes or response variables; such as, the unit of measurement, upper and lower acceptance criteria, and the order the attributes are to be presented in the stability summary report. A complete list of the preferred and other available options through the ATTRIBUTES dataset is given in Table 6. The attribute information is passed to BIGSTEP as the value of SAS® variables in the ATTRIBUTES dataset through the IN_DATA_ATTRIBUTES option in the % BIGSTEP call to the macro library.

The dataset ATTRIBUTES can be defined in two ways; either as part of the analysis program, or as a permanent SAS® dataset referenced in the analysis program. As an example, the ATTRIBUTES dataset is defined in the analysis program given in Table 4. The names used for the default variables ATTRIBUTE and STORAGE in the RESPONSES dataset must be the same used in the ATTRIBUTES dataset. Not all options available through the ATTRIBUTES dataset need to be specified. Variable labels and formats cannot be set in the ATTRIBUTES dataset.

Alternatively, for those options that are to be used repeatedly for several stability analyses, ATTRIBUTES can be defined as a permanent SAS® dataset, stored in a convenient directory. The format of the ATTRIBUTES dataset follows conventional SAS® dataset formatting. An example of an ATTRIBUTES dataset is given in Table 5. A LIBNAME needs to be created in the analysis program, or one of the existing LIBNAMEs, can be used if the permanent ATTRIBUTES dataset is stored in the appropriate directory. The permanent dataset ATTRIBUTES is then referenced in the analysis program in a dataset statement, similar to the data statement in the example analysis program in Table 4. Similar to the example analysis program in Table 4, additional ATTRIBUTES options can be defined in the dataset statement.

TABLE 4

Example Dataset Format for ATTRIBUTES

| ATTRIBUTE | IN_LEVEL_UNIT | IN_ACCEPT_LL | IN_ACCEPT_UL | IN_ANALYTICAL_PROCEDURE |
|---|---|---|---|---|
| ASSAY | % | 90 | 105 | HPLC |
| IMP | % | — | 0.5 | |
| WATER | pap | 25 | 37 | |
| ... | | | | |

| ATTRIBUTE | IN_ATTRIBUTE_SORT | IN_ATTRIBUTE_DEC |
|---|---|---|
| ASSAY | 2 | 2 |
| IMP | 1 | 3 |
| WATER | 3 | 0 |
| ... | | |

TABLE 5

Options for Dataset ATTRIBUTES

| Variable | Mandatory | Type | Description | Comments |
|---|---|---|---|---|
| ATTRIBUTE | yes | same as in analysis dataset | name of attribute to be evaluated | values must not be missing values must be the same as in RESPONSES dataset |
| IN_LEVEL_UNIT | yes | char | attribute measurement unit | |
| IN_ACCEPT_LL | no | num | lower acceptance criterion for attribute | IN_ACCEPT_LL or IN_ACCEPT_UL must be defined if IN_ACCEPT_LL and IN_ACCEPT_UL are stated, LL must be less than UL. |
| IN_ACCEPT_UL | no | num | upper acceptance criterion for attribute | IN_ACCEPT_LL or IN_ACCEPT_UL must be defined if IN_ACCEPT_LL and IN_ACCEPT_UL are stated, LL must be less than UL |
| IN_REF_LINE1 | no | num | additional horizontal reference line in graphs line is displayed in every graph | |
| IN_REF_LINE1_DESC | no | char | label for IN_REF_LINE1 | only relevant if IN_REF_LINE1 is stated |
| IN_REF_LINE2 | no | num | additional horizontal reference line in graphs line is displayed in every graph | |
| IN_REF_LINE2_DESC | no | char | label for IN_REF_LINE2 | only relevant if IN_REF_LINE2 is stated |
| IN_REF_POS | no | char | position for label of reference line | must be defined, if IN_REF_LINE1/2 and IN_REF_LINE1/2_DESC are stated valid values: LEFT\|RIGHT |
| IN_ANALYTICAL_PROCEDURE | no | char | analytical procedure | |
| IN_ATTRIBUTE_SORT | no | num | ATTRIBUTE presentation order for summary results output if not stated, order is the same as in the analysis dataset | |
| IN_ATTRIBUTE_DEC | yes | num | number of decimal places in summary results used for raw data values for summary statistics (mean, standard deviation, confidence limits, prediction limits, tolerance limits), one additional decimal place is used calculations are performed without rounding | valid values: 0 <= Integer <= 8. |

An optional GROUPS dataset may contain the information about the statistical analysis to be conducted for each attribute or response variable as well as which summary information should be provided; such as, the regression model to characterize the response variable or if the pre-test results on the response trend in the data are to be reported. The GROUPS dataset is only necessary if the user wants to define different settings for different attributes, for example, different functions should be used. A complete list of the options available through the GROUPS dataset is given in Table 6. The analysis information for each response variable is passed to BIGSTEP as the value of SAS® variables in the GROUPS dataset through the IN_DATA_GROUPS option in the % BIGSTEP call to the macro library.

The dataset GROUPS can be defined in two ways; either as part of the analysis program, or as a permanent SAS® dataset referenced in the analysis program. The GROUPS dataset is defined in the example analysis program given in Table 4. Not all options available through the GROUPS need to be specified.

Alternatively, for those options that are to be used repeatedly for several stability analyses, GROUPS can be defined as a permanent SAS® dataset, stored in a convenient directory. The format of the GROUPS dataset follows conventional SAS® dataset formatting. An example of a GROUPS dataset is given in Table 7. A LIBNAME needs to be created in the analysis program, or one of the existing LIBNAMEs, can be used if the permanent GROUPS dataset is stored in the appropriate directory. The permanent dataset GROUPS is then referenced in the analysis program in a dataset statement, similar to the data statement in the example analysis program in Table 4. Similar to the example analysis program in Table 4, additional GROUPS options can be defined in the dataset statement.

TABLE 6

Example Dataset Format for GROUPS

| ATTRIBUTE | STORAGE | GL_FUNCTION | GL_MODEL | GL_EXTRAPOLATION_LIMIT |
|---|---|---|---|---|
| ASSAY | 25° C./60% RH | EXP1 | | |
| ASSAY | 30° C./70% RH | EXP1 | | |
| ASSAY | 40° C./75% RH | EXP1 | | 24 |
| IMP | 25° C./60% RH | | | |
| IMP | 30° C./70% RH | | | |
| IMP | 40° C./75% RH | | M_1_1 | 24 |
| ASSAY | 25° C./60% RH | EXP1 | | |
| ASSAY | 30° C./70% RH | EXP1 | | |
| ASSAY | 40° C./75% RH | EXP1 | | 24 |
| IMP | 25° C./60% RH | | | |
| IMP | 30° C./70% RH | | | |
| IMP | 40° C./75% RH | | M_1_1 | 24 |

| ATTRIBUTE | OUTG_XAXIS_END | OUTG_XAXIS_BY | OUTG_XAXIS_MINOR |
|---|---|---|---|
| ASSAY | | | |
| ASSAY | | | |
| ASSAY | 25 | 3 | 2 |
| IMP | | | |
| IMP | | | |
| IMP | 25 | 3 | 2 |
| ASSAY | | | |
| ASSAY | | | |
| ASSAY | 25 | 3 | 2 |
| IMP | | | |
| IMP | | | |
| IMP | 25 | 3 | 2 |

TABLE 7

Options for Dataset GROUPS

| Variable | Mandatory | Type | Description | Comments |
|---|---|---|---|---|
| <BYVAR> | yes (if BYVAR is used in analysis dataset) | same as analysis dataset | levels of variable to be analyzed separately defined by parameter IN_BY_VARS | defines data group to be evaluated values must be the same as in RESPONSES dataset |
| ATTRIBUTE | yes | same as analysisdataset | name of attribute to be evaluated | defines data group to be evaluated values must be the same as in RESPONSES dataset |
| STORAGE | yes | char | storage condition | defines data group to be evaluated values must be the same as in RESPONSES dataset |
| DDT_SELECT DDA_SELECT DDG_SELECT DDS_SELECT TRC_SELECT PPC_SELECT PTC_SELECT SLC_SELECT | no | char | Selection of output displays for single groups. If for example TRC_SELECT is switched to NO for all groups (attributes, by-groups) of storage condition 5°, the time response displays are not created for these storage condition groups. All displays selected by parameters GL_DISPLAYS (and GL_SHORT_REPORT) are created despite of the displays deselected here. | Only relevant if the respective or related display is selected. The values must be YES/NO/Y/N (case insensitive) or empty. Only NO/N has the deselection effect for the considered group. YES/Y has the same meaning as missing. |
| GL_FUNCTION | no | char | User defined types of regression functions for pooling process, pre-test and shelf life calculations, overwrites homonymous parameter for the considered group. | Same valid values as the parameter. |
| GL_MODEL | no | char | User defined model for shelf life calculations, overwrites homonymous parameter for the considered group. | Same valid values as the parameter. |
| GL_EXTRAPOLATION_LIMIT | no | num | Extrapolation limit, overwrites homonymous parameter for the considered group. | Same valid values as the parameter. |

TABLE 7-continued

Options for Dataset GROUPS

| Variable | Mandatory | Type | Description | Comments |
| --- | --- | --- | --- | --- |
| SLC_PROPOSED_SL | no | num | Proposed shelf life, overwrites homonymous parameter for the considered group. must be set. | If the general parameter SLC_PROPOSED_SL is not set, either all or none of the values For all groups, SLC_PROPOSED_SL <= GL_EXTRAPOLATION_LIMIT must be satisfied. Same valid values as the parameter. |
| OUTG_XAXIS_END | no | num | X-axis end, overwrites homonymous parameter for the considered group. The variable is only relevant for graphs. | Same valid values as the parameter. |
| OUTG_XAXIS_BY | no | num | Distance between major ticks of x-axis, overwrites homonymous parameter for the considered group. The variable is only relevant for graphs. | Same valid values as the parameter. |
| OUTG_XAXIS_MINOR | no | num | Number of minor ticks for x-axis, overwrites homonymous parameter for the considered group. The variable is only relevant for graphs. | Same valid values as the parameter. |
| OUTG_YAXIS_START | no | num | Y-axis start, user defined. Usually, y-axis start is calculated automatically with use of response values and lower acceptance criterion (if present). The variable is only relevant for graphs. | If any graph display is selected, OUTG_YAXIS_START, OUTG_YAXIS_END and OUTG_YAXIS_BY must all be set or all be empty. OUTG_YAXIS_START must be less than OUTG_YAXIS_END. |
| OUTG_YAXIS_END | no | num | Y-axis end, user defined. Usually, y-axis end is calculated automatically with use of response values and upper acceptance criterion (if present). The variable is only relevant for graphs. | |
| OUTG_YAXIS_BY | no | num | Distance between major ticks of y-axis. The variable is only relevant for graphs. | |
| OUTG_YAXIS_MINOR | no | num | Number of minor ticks for y-axis. If nothing is defined, 1 minor tick is the default. The variable is only relevant for graphs. | Same valid values as the parameter. |

The CONSTANTS dataset (see Table 8) is a SAS® dataset required by BIGSTEP. By default, the CONSTANTS dataset is assumed to be stored in the directory referenced by LIBNAME BIGSTEP and named CONSTANTS. This background dataset listing the three variables ID, VALUE, and COMMENT (see Table 9) defines the values for constant texts like table headers or line descriptions in graphs used by BIGSTEP and should not be changed.

If a change of constants is necessary the corresponding text in variable VALUE must be changed. For texts defining a column header or column content, the '$'-sign can be used for indicating line breaks. The variable ID is used as identification of the constant and must not be changed. Only the defined IDs are used by the macro. If an expected ID as for example 'AC' cannot be found in the datasets the macro uses the default ID instead of the VALUE and prints a message in the LOG.

The CONSTANTS defaults can be changed in three ways:

The settings in the CONSTANTS dataset are changed and the modified dataset is resaved

TABLE 8

Variables of Dataset CONSTANTS

| Variable | Mandatory | Type | Description | Value check |
| --- | --- | --- | --- | --- |
| ID (Identifier) | yes | Char | Identification of the constant. | Must not be empty. |
| VALUE | yes | Char | Value, which is substituted for the constant | Must not be empty. |
| COMMENT | no | Char | Comment with description of relevance | |

A second permanent dataset with a different name is created and referenced in the IN_SYSTEM_CONSTANTS option through the BIGSTEP macro call A temporary dataset is used and referenced in IN_SYSTEM_CONSTANTS However, BIGSTEP was designed to be a globally harmonized stability analysis program, providing a consistent shelf life analysis and summary report. By changing the contents of that background SAS® datasets, that consistency cannot be maintained and is thus not preferred.

TABLE 9

Options for Dataset CONSTANTS

| Identification | Value | Comment |
|---|---|---|
| AC | Acceptance$criteria | Column header for acceptance criteria (Different tables) |
| AP | Analytical$procedure | Column header for analytical procedure (DDT, DDS) |
| SC | Storage$condition | Column header for storage condition (Different tables) |
| OBS | Obs. | Column header for observation number (DDT) |
| TIME | Time [{time-unit}] | Common column header for all time columns (DDT) |
| MISSVALUE | n.d. | Content for missing values in input dataset (DDT) |
| STATS | Summary$statistics | Column header for names of statistics (N, Mean, . . . ) (DDS) |
| N | N | Column header, row description for N (DDS) |
| MEAN | Mean | Column header, row description for mean (DDS) |
| SD | SD | Column header, row description for standard deviation (DDS) |
| NC | not calc. | If statistics cannot be calculated because N <= 1, this text is displayed (DDS). If data are constant and shelf life cannot be calculated, this text is displayed (SLS). |
| CV | CV | Row description for coefficient of variation (DDS) |
| MIN | Min | Row description for minimum (DDS) |
| MAX | Max | Row description for maximum (DDS) |
| RF | Regression$function | Column header for regression function (TRT) |
| MDF | Model$DF | Column header for degrees of freedom for model (TRT) |
| EDF | Error$DF | Column header for degrees of freedom for error (TRT) |
| SSE | SSE | Column header for sum of squares error (TRT) |
| MSE | MSE | Column header for mean squares error (TRT) |
| CONV | Converge$status | Column header for convergence status (Yes/No) (TRT) |
| CONV_YES | Yes | Column content for convergence status is case of convergence (TRT) |
| CONV_NO | No | Column content for convergence status is case of convergence (TRT) |
| LIN | Simple linear | TRG-Graph title, TRT name for linear time response relationship (TRG, TRT) |
| QUAD | Quadratic | TRG-Graph title, TRT name for quadratic time response relationship (TRG, TRT) |
| CUB | Cubic | TRG-Graph title, TRT name for cubic time response relationship (TRG, TRT) |
| EXP1 | Exponential 1 | TRG-Graph title, TRT name for exponential 1 time response relationship (TRG, TRT) |
| EXP2 | Exponential 2 | TRG-Graph title, TRT name for exponential 2 time response relationship (TRG, TRT) |
| EXP3 | Exponential 3 | TRG-Graph title, TRT name for exponential 3 time response relationship (TRG, TRT) |
| MODEL | Model | Column header for model |
| SOURCE | Source of$variability | Column header for source in pooling process table, if table type is "ANCOVA" (PPT) |
| INTERCEPTS | Intercepts | Column content for main-factor dependent intercepts in table type "ANCOVA" (PPT) |
| OVERALL_SLOPE | Overall slope | Column content for common slope source in table type "ANCOVA" (PPT) |
| SLOPES | Slopes | Column content for independent slope source in table type "ANCOVA" (PPT) |
| RESIDUAL | Residual | Column content for ERROR source in table type "ANCOVA" (PPT) |
| DF | DF | Column header for degrees of freedom (PPT, PTT) |
| FV | F value | Column header for F value (PPT) |
| PV | p value | Column header for p value (PPT, PTT) |
| ALPHA | {alpha} | Column header for alpha (PPT). If possible, the greek symbol is used. |
| POOLING | Pooling | Column header for pooling (Yes or No) (PPT) |
| POOLING_COMMON | common | Column content for positive pooling decision in table type "ANCOVA" (PPT) |
| POOLING_IND | individual | Column content for negative pooling decision in table type "ANCOVA" (PPT) |
| POOLING_YES | Yes | Column content for positive pooling decision in table type "F-tests" (PPT) |

TABLE 9-continued

Options for Dataset CONSTANTS

| Identification | Value | Comment |
|---|---|---|
| POOLING_NO | Rejected | Column content for negative pooling decision in table a "F-tests" (PPT) |
| SLOPE | Slope | Column header for slope (PTT) |
| SE | Standard$error | Column header for standard error (PTT) |
| TV | t value | Column header for t value (PTT) |
| COT | Change$over time | Column header for change over time (Yes/No) (PTT) |
| COT_YES | Yes | Column content for decision: Change over time |
| COT_NO | No | Column content for decision: No change over time |
| POOLED | Pooled | Column content for use in MF/AF columns, if pooling is possible (PTT) |
| CI_TMAX | {conf-level} Confidence$interval at tmax | Column header for confidence interval at maximum extrapolation time (SLT, SLS) |
| CI_PROPSL | {conf-level} Confidence$interval at$proposed shelf life | Column header for confidence interval at proposed shelf life (SLT, SLS) |
| PI_TMAX | {conf-level} Prediction$interval at tmax | Column header for prediction interval at maximum extrapolation time (SLT, SLS) |
| PI_PROPSL | {conf-level} Prediction$interval at$proposed shelf life | Column header for prediction interval at proposed shelf life (SLT, SLS) |
| TI | {conf-level} Tolerance$interval$({coverage} coverage) | Column header for tolerance interval (SLT, SLS) |
| SUPPORTED | Supported | Column header for supported (yes/no) column (SLT) |
| SUPPORTED_YES | Yes | Column content for lines, where shelf life can be supported. (SLT) |
| SUPPORTED_NO | No | Column content for lines, where shelf life cannot be supported. (SLT) |
| CI_TYPE | Confidence | Text containing only the interval type (CI) |
| TI_TYPE | Tolerance | Text containing only the interval type (TI) |
| PI_TYPE | Prediction | Text containing only the interval type (PI) |
| INTERCEPT | Intercept | Column header for coefficient INTERCEPT (SLT) |
| BETA | {beta} | Column header for coefficient beta (SLT) |
| GAMMA | {gamma} | Column header for coefficient gamma (SLT) |
| MAXTIME | Maximum$extrapolation$time (tmax)$[{time-unit}] | Column header for maximum extrapolation time (SLT, SLS) |
| PROPTIME | Proposed$shelf life$ [{time-unit}] | Column header for proposed shelf life time (SLT, SLS) |
| SL | Shelf life$[{time-unit}] | Column header for calculated shelf life (SLT) |
| NOCOT | No change over time | Text displayed in shelf life column if pretest indicated no change over time (SLS) |
| CONSTANT | constant | Text displayed in model column if SD < 10e−6 (SLS) |
| GRAPH_AC_LL | Acceptance criterion | By change of these constants, the labeling of the acceptance criterion line can be influenced relevant for all graphs) |
| GRAPH_AC_DL | Acceptance criterion | |
| LANDSCAPE_MARGIN_UPPER | 2.54 | Margins depending on paper orientation defined by parameter OUT_ORIENTATION (unit is cm!) |
| LANDSCAPE_MARGIN_LOWER | 2.54 | |
| LANDSCAPE_MARGIN_LEFT | 3.42 | |
| LANDSCAPE_MARGIN_RIGHT | 3.42 | |
| PORTRAIT_MARGIN_UPPER | 3.42 | |
| PORTRAIT_MARGIN_LOWER | 3.42 | |
| PORTRAIT_MARGIN_LEFT | 2.54 | |
| PORTRAIT_MARGIN_RIGHT | 2.54 | |
| PAPER_FORMAT | A4 | All values NE A4 are interpreted as letter... A4 format is: 21 * 29.7 cm Letter format is: 21.59 * 27.94 cm By use of the paper format and the margins, the size of the graphs is calculated. |

The DEFAULTS dataset is a SAS® dataset required by BIGSTEP. By default, the DEFAULTS dataset is assumed to be stored in the directory referenced by LIBNAME BIGSTEP and named DEFAULTS. This background dataset listing the three variables PARAMETER, DEFAULT, and COMMENT defines the default settings for every BIGSTEP analysis and output option.

If a change of the parameter setting is necessary due to a particular stability analysis or specific report requirements, they can be changed in the BIGSTEP macro call, as in the analysis program shown in Table 4. In case a modified option is to be used repeatedly for various stability analyses, it might be more convenient to change the default setting in the dataset DEFAULTS or to use a modified dataset containing the needed defaults.

The defaults of the DEFAULTS dataset can be changed in four ways:
  The settings in the DEFAULTS dataset are changed and the modified dataset is resaved
  A second permanent dataset is created and referenced in the IN_SYSTEM_DEFAULTS option through the BIGSTEP macro call
  A temporary dataset is used and referenced in IN_SYSTEM_DEFAULTS By changing the parameter options in the BIGSTEP macro call Again by changing the contents of that background SAS® datasets, consistency cannot be maintained. Thus, this is not preferred.

The GRAPHS dataset (see Table 10) is a SAS® dataset required by BIGSTEP. By default, the GRAPHS dataset is assumed to be stored in the directory referenced by LIBNAME BIGSTEP and named GRAPHS. This background dataset listing the variables ELEMENT, SYMBOL, SYMBOL_FONT, SYMBOL_VALUE, SYMBOL_HEIGHT, LINE, LINE_HEIGHT, and COLOR (see Tables 11-13) defines the defaults for the graph options used by BIGSTEP to produce the graphs in the file format EMF (Enhanced Windows Metafile). It is intended that this dataset is to be modified to accommodate the requirements of the statistical analysis and study report.

TABLE 10

Default GRAPHS Dataset

| ELEMENT | SYMBOL | SYMBOL_FONT | SYMBOL_VALUE | SYMBOL_HEIGHT | LINE | LINE_HEIGHT | COLOR |
|---|---|---|---|---|---|---|---|
| AC | | | | — | 21 | 1 | red |
| REFLINE | | | | — | 5 | 1 | green |
| INTERVAL | | | | — | 4 | 1 | black |
| SINGLELINE | DOT | | | 4 | 1 | 1 | blue |
| DATA1 | | WINGDINGS | '8C'x | 9 | 1 | 1 | blue |
| DATA2 | | WINGDINGS | '8D'x | 9 | 1 | 1 | green |
| DATA3 | | WINGDINGS | '8E'x | 9 | 1 | 1 | red |
| DATA4 | | WINGDINGS | '8F'x | 9 | 1 | 1 | black |
| DATA5 | | WINGDINGS | '90'x | 9 | 1 | 1 | gray |
| DATA6 | | WINGDINGS | '91'x | 9 | 1 | 1 | cyan |
| DATA7 | | WINGDINGS | '92'x | 9 | 1 | 1 | red |

TABLE 11

Variable Definitions for Dataset GRAPHS

| Variable | Mandatory | Type | Description | Comments |
|---|---|---|---|---|
| ELEMENT | yes | char | graph element to be formatted | the following elements (rows) must be defined: AC, REFLINE, INTERVAL, SINGLELINE<br>additional elements are DATA<n> |
| SYMBOL | yes | char | SAS ® symbol used for ELEMENT | values can be DOT, CIRCLE, etc. |
| SYMBOL_FONT<br>SYMBOL_VALUE | yes | char | font and value used for ELEMENT | if SYMBOL is specified, SYMBOL_FONT and SYMBOL_VALUE must both be missing<br>SYMBOL_FONT and SYMBOL_VALUE must both be missing or both be specified |
| SYMBOL_HEIGHT | yes | num | height of symbol used for ELEMENT | must not be missing if SYMBOL or SYMBOL_FONT is specified<br>specified in point size<br>symbol size is used for mean values and individual data<br>if a graph contains mean values and individual data, the individual data are displayed smaller |
| LINE | yes | num | SAS ® line type used for ELEMENT | must be specified |
| LINE_HEIGHT | yes | num | height of line used for ELEMENT | must be specified<br>specified in point size |
| COLOR | yes | char | color used for ELEMENT | must be specified |

The GRAPHS defaults can be changed in three ways:
The settings in the GRAPHS dataset are changed and the modified dataset is resaved
A second permanent dataset with a different name is created and referenced in the IN DATA_GRAPHS option through the BIGSTEP macro call
A temporary dataset is used and referenced in IN_DATA_GRAPHS However, it is again preferred to provide consistency that the settings not be changed.

TABLE 12

Definition of Symbols and Lines

| Graphical element | Comment |
|---|---|
| AC | In all graphs, all lines for acceptance criteria are plotted with the defined line layout given in the observation identified by AC. |
| INTERVAL | In all graphs, all intervals (PI, CI or TI) are plotted with the defined line layout given in the observation identified by INTERVAL. |
| SINGLELINE | In all graphs, which plot only one line (e.g., regression line or curve, interpolation line) this is plotted with the defined line and symbol layout given in the observation identified by SINGLELINE. |
| REFLINE | In all graphs, all reference lines (defined in the dataset ATTRIBUTES) are plotted with the defined line layout given in the observation identified by REFLINE. |
| DATA<n> | In all graphs that plot more than one line/symbol, these are plotted with the defined line and/or symbol layout given in the observation identified by DATA<n>. For each line <n> one DATA<n> is used (one by one). If there are not enough DATA<n> observations available, which is possible in the case of many main factor levels and/or additional factor levels, the macro uses the defined layout values again. |

The BIGSTEP statistical analysis to be conducted and the format of the summary output report are controlled through a series of program options. Each option is listed in the DEFAULTS permanent SAS® dataset. Where appropriate, a default is set for many of the options, noted in the option definition below. The option default can be changed by specifying the change in either a temporary dataset in the analysis program, named DEFAULT, or permanent DEFAULT SAS® dataset, or specified in the % BIGSTEP call to the macro library.

Although the invention provides methods and apparatus which allow more harmonized stability reports the shown default tables and graphs can be modified as described in the additional information lists of this chapter to satisfy user and site specific requirements. For example, it is possible to produce separate tables for each evaluation group (level of by-group, attribute, and storage condition) instead of including all information as identifying columns in the output result table.

The invention can be applied to stability data for different combinations of
Attributes
(e.g., Assay, Impurities)
Additional factor levels
(e.g., levels of storage orientation like 'Upright' and 'Inverted')
Storage conditions
(e.g., 25° C./60% RH, 30° C./70% RH)
By-variables
(combinations of the levels of different by-variables are called by-groups)
The main functions of invention are:
Group DD
Presentation of individual data and summary statistics
Group TR
Comparison of different time-response relationships Group PP
Model selection by pooling of batches and additional factor levels
Use of common release data in pooling process
Use of different time-response relationships in pooling process
Group PT
Pre-test to test if a formal statistical analysis is necessary Group SL
Shelf-life calculations with one- or two-sided confidence or prediction intervals
Support of proposed shelf life The FIG. 2 flow chart is an overview of the integrated functionalities. The individual data to be evaluated must be given as an SAS® dataset. A representative evaluation could follow the stages of the flow chart. After a descriptive analysis (DD) with individual data tables, summary statistic tables, and graphs, different time-response relationships are compared (TR) and the user has to decide which time-response relationship is used in the following process. The pooling process (PP) selects the most appropriate regression model. With respect to this model a pre-test (PT) can be conducted. If the pre-test is chosen, the system decides dependent on the change over time to stop the formal evaluation or to move on. If either the result of the pre-test is that there is a change over time or if otherwise the pre-test is not chosen the shelf life (SL) is calculated. All results can be presented in tables and graphs and transferred to, e.g., a Word file.

If the aim is to support a given shelf life, the program first checks whether the pre-defined proposed shelf life can be supported with the start model individually per batch and additional factor. This check is performed with pre-test and shelf life calculation (without pooling). If the shelf life cannot be supported, pooling is performed (pooling can be limited to a given level) and pre-test and shelf life calculation are calculated again with the pooled model.

Since the estimated shelf lives are usually longer when the data basis is broader, the aim of the pooling process is to combine data from different batches (main factor levels) and/or different levels of the additional factor, for example, storage orientation or package material. The storage conditions are not considered in the pooling process, the analyses are always performed separately for the different storage conditions.

The pooling process is a hierarchical process in order to identify for an attribute across main factor levels or additional factor levels the most parsimonious system of equations to characterize change in response. Starting with a model fitting individual coefficients for each batch or additional factor (most complex model) the system checks step by step the 'poolability' of coefficients across batches or additional factors.

The invention is amenable to pooling strategies for several situations where the number of models included in the pooling process is defined by the design and evaluation strategy of the study.

Number of considered models in the pooling process is defined by two study design questions:
  Is an additional factor to batch considered for pooling or not?
    Defined by parameter. IN_ADD_FACTOR
  Are common release data used or not?
    Defined by parameter: GL_COMMON_RELEASE Number of considered models in the pooling process is defined by two study evaluation strategy questions:
  Are slopes tested before intercepts (pooling without order) or not?
    Defined by parameter: PPC_SLOPES_FIRST
  Is the additional factor considered for pooling before batch?
    Defined by parameter: PPC_AF_FIRST The different combinations of these criteria define the number of models considered in the pooling process. The sections, charts, and plots in the User's Manual depict the strategy for the simple linear approach indicating the possible paths for the pooling process from the highest most complex model to the lowest model with just one regression line (polled for slopes and intercepts).

Before a stability data evaluation is started several data and parameter checks to avoid an incorrect use are performed. If the data are not appropriate, the parameter settings inconsistent or incomplete the program according to the invention can produce detailed ERROR and WARNING messages, which are described in this chapter. An ERROR message usually stops the macro whereas a WARNING does not. If an ERROR-message appears, the detailed information given helps to find the cause of the problem. After solving the problem by modification of the data or parameter setting the program can be started again.

For parameter check, the macro performs the following steps:
  1. Setting of all empty parameters to default
  2. Setting of all parameters with value NONE to empty
  3. Start of parameter check and processing Thus, if one wants to set a parameter to empty, NONE has to be used. For example: DDS_TITLE3 should be set to empty the syntax DDS_TITLE3=NONE instead of DDS_TITLE3=must be defined. Otherwise BIGSTEP uses the default setting.

Usually, the parameters are upcased and dequoted. Titles, footnotes, and filenames are typical examples for case sensitive parameters.

The parameter checks are:
  1. Check, whether all mandatory parameters are filled
  2. Check, whether all conditional mandatory parameters are filled, if the condition is true
  3. Check, whether parameter contents and parameter combinations are valid If possible, parameter checks are performed only if they are necessary. Therefore, the parameter GL_DISPLAYS must be checked very early since the value of this parameter defines whether other parameters are conditional mandatory or not.

The parameter check handles as many parameters as possible. If several parameters with invalid values are handed over to the macro, various error messages appear. If the check of a main parameter such as GL_DISPLAYS fails, the macro cannot check all given parameters because many parameters are dependent on the chosen displays.

In case of severe errors as for example invalid values for parameters or missing information in datasets, the macro stops with error message(s).

Figure 1:
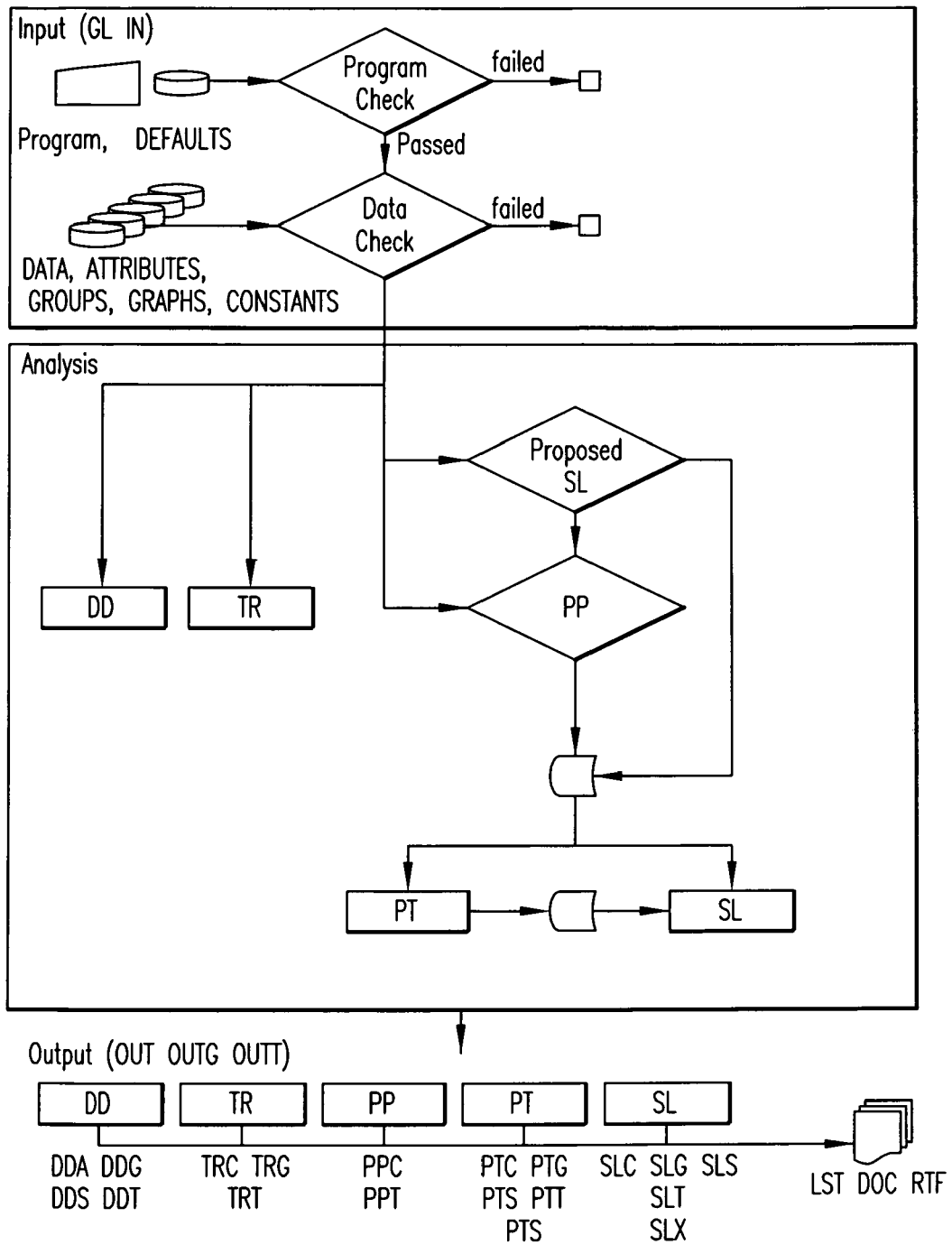
FIG. 1 is a schematic flow chart of the BIGSTEP analysis.
Figure 2:
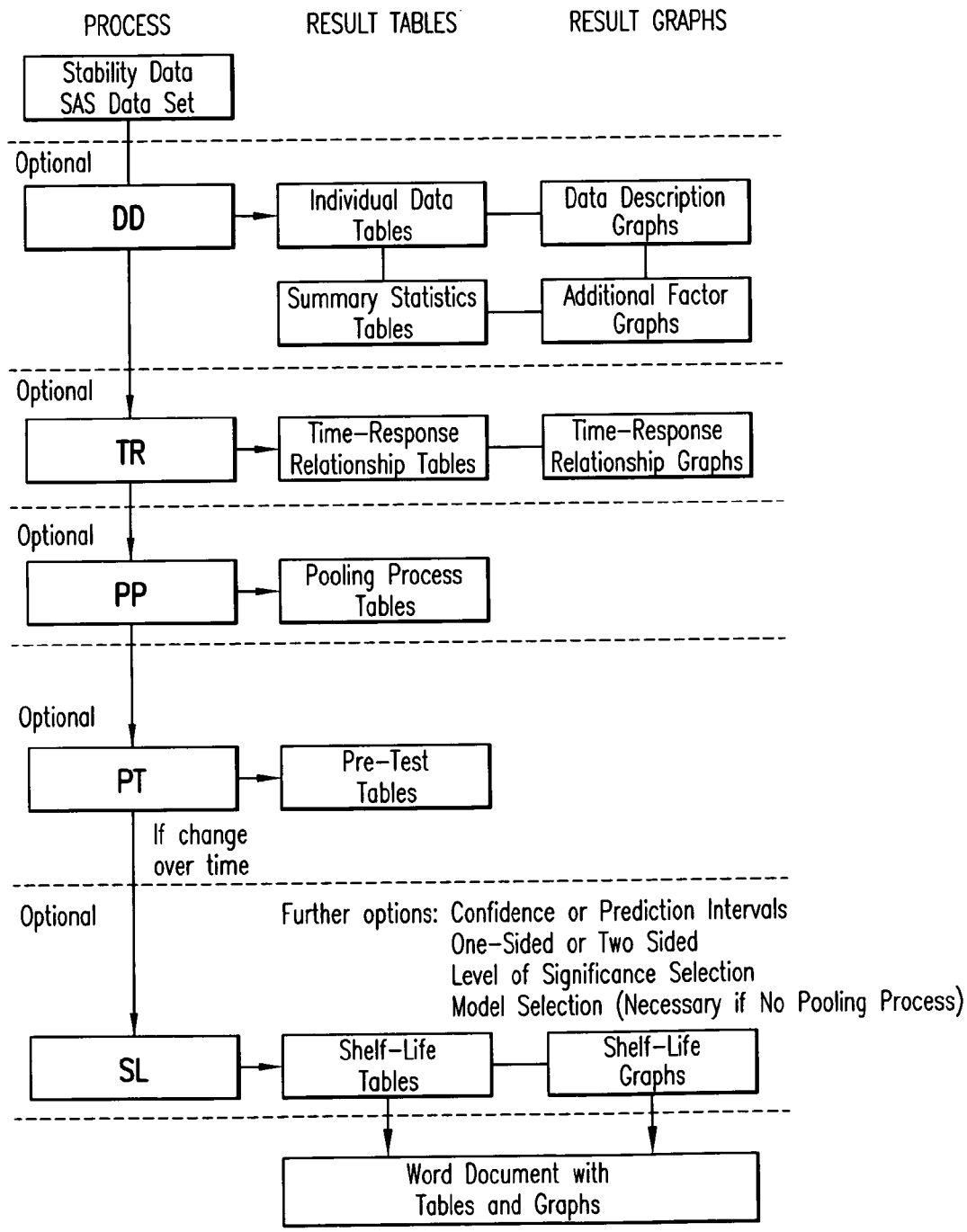
FIG. 2 flow chart is an overview of the integrated functionalities of the program.

We claim:

1. A computer-implemented method using a macro integrated into statistical analysis software for statistical analysis and summarization of a stability study on a pharmaceutical product which comprises,
  inputting and summarizing data observed for a stability study on a pharmaceutical product,
  statistically analyzing the data, including using at least one regression function to characterize the time-response relationship of at least one stability response variable and, to estimate a shelf life of the pharmaceutical product or confirm the shelf life of an existing pharmaceutical product, and
  providing standardized output data and graphical presentations of observed stability response data.

2. The method of claim 1, wherein the standardized output data and graphical presentations are output in a format suitable for standard word-processing documents.

3. The method of claim 1, further comprising performing a statistical analysis to test the consistency of response among different batches and/or among the levels of at least one additional stability factor variable.

4. The method of claim 3, wherein the at least one additional stability factor variable is product orientation or product packaging.

5. The method of claim 1, wherein the shelf life is estimated based on user supplied specification limits or acceptance criteria and using an automated best fitted or user defined regression function.

6. The method of claim 1, further comprising automated pooling of batch or additional study factor response data following a pre-defined pooling strategy.

7. The method of claim 1, wherein the statistical analysis is conducted using analyses of covariance techniques by fitting any desired confidence or prediction interval for mean responses represented by regression lines or curves.

8. The method of claim 1, wherein the standardized output data and graphical presentations are output in a format suitable for direct insertion into a statistical or study report acceptable for submission to a regulatory agency for pharmaceutical product approval.

9. The method of claim 1, wherein the macro is implemented using the same language and commands used with the statistical analysis software.

10. The method of claim 1, wherein the macro connects the data to be analyzed and defines particular options for the statistical analysis of the data and defines the output data and graphical presentation requirements.

11. The method of claim 1, wherein statistical analysis of data from several response variables and storage conditions are conducted in one run.

12. The method of claim 1, wherein the statistical analysis includes analyses of: attributes of the pharmaceutical product including assay and impurity attributes; additional factor levels including levels of storage orientation of the pharmaceutical product; and storage conditions of the pharmaceutical product.

13. The method of claim 1, wherein the statistical analysis includes comparing of different time-response relationships.

14. The method of claim 1, wherein the statistical analysis includes model selection by pooling of batches and additional factor levels, use of common or independent release data in a pooling process and use of different time-response relationships in a pooling process.

15. The method of claim 1, wherein the statistical analysis and output includes graphical comparison of six non-linear time-response functions in a table with a listing of the functions ranked by the best fitting.

16. The method of claim 1, wherein the statistical analysis uses the following four linear and non-linear functions: simple linear, quadratic, first order exponential and second order exponential, for the statistical analysis of stability data.

17. The method of claim 1, which includes providing or performing: data description, a time response regression model, a pooling process for the regression model, a pre-test evaluation and/or shelf life estimation.

18. The method of claim 17, wherein: the data description includes providing data listings, summary statistics, and plots of the observed data; the time response regression model includes analysis of different regression model fits to the observed response data; and the pre-test evaluation includes a determination if there is a significant change in response over storage time.

19. A computer loaded with a general statistical analysis software and a macro integrated with the software such that the computer is capable of performing the computer-implemented method according to claim 1 using the software and macro.

20. A computer loaded with a general statistical analysis software and a macro integrated with the software such that the computer is capable of performing the computer-implemented method according to claim 2 using the software and macro.

21. A computer loaded with a general statistical analysis software and a macro integrated with the software such that the computer is capable of performing the computer-implemented method according to claim 3 using the software and macro.

22. A computer loaded with a general statistical analysis software and a macro integrated with the software such that the computer is capable of performing the computer-implemented method according to claim 5 using the software and macro.

23. A computer loaded with a general statistical analysis software and a macro integrated with the software such that the computer is capable of performing the computer-implemented method according to claim 6 using the software and macro.

24. A computer loaded with a general statistical analysis software and a macro integrated with the software such that the computer is capable of performing the computer-implemented method according to claim 7 using the software and macro.

25. A computer loaded with a general statistical analysis software and a macro integrated with the software such that the computer is capable of performing the computer-implemented method according to claim 8 using the software and macro.

26. A computer loaded with a general statistical analysis software and a macro integrated with the software such that the computer is capable of performing the computer-implemented method according to claim 9 using the software and macro.

27. A computer loaded with a general statistical analysis software and a macro integrated with the software such that the computer is capable of performing the computer-implemented method according to claim 10 using the software and macro.

28. A computer loaded with a general statistical analysis software and a macro integrated with the software such that the computer is capable of performing the computer-implemented method according to claim 11 using the software and macro.

29. A computer loaded with a general statistical analysis software and a macro integrated with the software such that the computer is capable of performing the computer-implemented method according to claim 12 using the software and macro.

30. A computer loaded with a general statistical analysis software and a macro integrated with the software such that the computer is capable of performing the computer-implemented method according to claim 13 using the software and macro.

31. A computer loaded with a general statistical analysis software and a macro integrated with the software such that the computer is capable of performing the computer-implemented method according to claim 14 using the software and macro.

32. A computer loaded with a general statistical analysis software and a macro integrated with the software such that the computer is capable of performing the computer-implemented method according to claim 15 using the software and macro.

33. A computer loaded with a general statistical analysis software and a macro integrated with the software such that the computer is capable of performing the computer-implemented method according to claim 16 using the software and macro.

34. A computer loaded with a general statistical analysis software and a macro integrated with the software such that the computer is capable of performing the computer-implemented method according to claim 17 using the software and macro.

35. The method of claim 1, wherein data is provided from a stability study on one or more potentially stability-limiting response variables of the pharmaceutical product over time, where the pharmaceutical product of interest is stored in environmentally stable conditions to meet regulatory guidelines over a definable period.

36. A computer loaded with a general statistical analysis software and a macro integrated with the software such that the computer is capable of performing the computer-implemented method according to claim 35 using the software and macro.

* * * * *